United States Patent [19]

Laico et al.

[11] Patent Number: 4,892,521
[45] Date of Patent: Jan. 9, 1990

[54] PROTECTIVE COVER FOR HYPODERMIC NEEDLE

[75] Inventors: Joseph P. Laico, New City; Joseph L. Molino, Valley Cottage, both of N.Y.

[73] Assignee: Lincoln Mills, Inc., New City, N.Y.

[21] Appl. No.: 227,756

[22] Filed: Aug. 3, 1988

[51] Int. Cl.$^4$ .............................................. A61M 5/32
[52] U.S. Cl. .................................... 604/192; 604/198; 604/263
[58] Field of Search ............... 604/198, 192, 187, 110, 604/263, 197, 196

[56] References Cited

U.S. PATENT DOCUMENTS

| | | | |
|---|---|---|---|
| 2,847,995 | 8/1954 | Adams | 604/198 |
| 3,134,380 | 5/1964 | Armao | 604/198 |
| 4,795,432 | 1/1989 | Karczmer | 604/198 X |

Primary Examiner—John D. Yasko
Attorney, Agent, or Firm—Chilton, Alix & Van Kirk

[57] ABSTRACT

A protective cover for a hypodermic needle employs a pair of guide rods for guiding a protective cap from a retracted position to an extended protective position for shielding the hypodermic needle. A guide member projects transversely from the needle base and forms a pair of apertures which receive and interact with the guide rods. The guide rods are fixed to a protective cap portion of the cover. A guide rod mechanism is also employed in connection with a retractable, foldable sheath embodiment. The protective cover assembly may also take the form of telescopic shield sections which lock in the extended protective position by means of a cooperative projection/groove locking engagement.

12 Claims, 3 Drawing Sheets

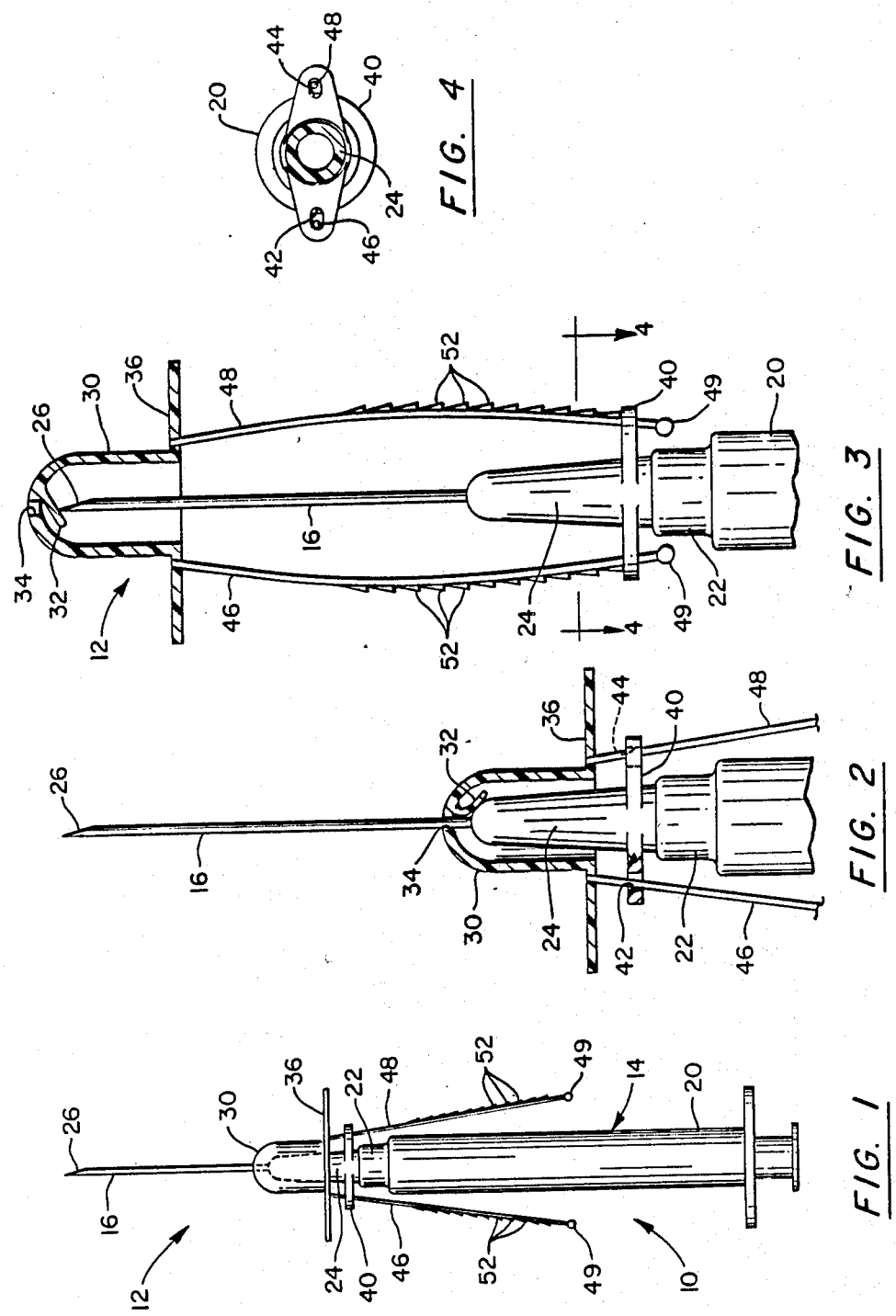

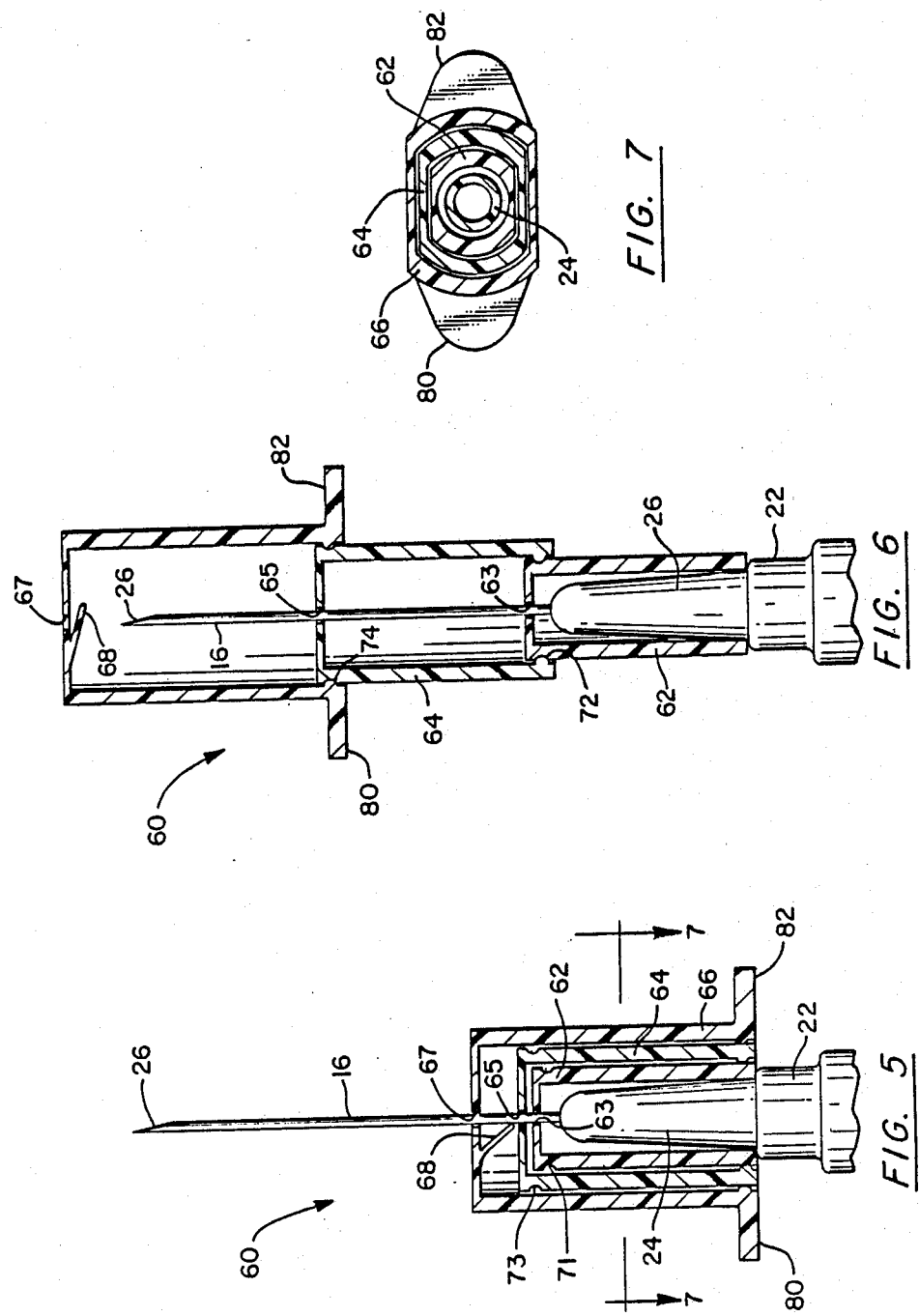

PROTECTIVE COVER FOR HYPODERMIC NEEDLE

BACKGROUND OF THE INVENTION

This invention relates generally to hypodermic needles and catheters which are adapted to inject substances into humans, animals, and/or to withdraw specimens therefrom. More particularly, the present invention relates generally to protective devices which are employed for shielding the needle of a hypodermic syringe, catheter or other injecting or withdrawing device after usage thereof.

The vast majority of hypodermic needles are disposable type needles which are discarded after usage. The shielding of the sharp end of the hypodermic needle is of critical concern to health practitioners both in relation to needle disposal and to handling the needle. Accidental exposure to the sharp end of the needle can have very serious and even fatal health consequences. For example, the needle may be contaminated with diseases such as hepatitis and AIDS. It is well documented that accidental puncture with a contaminated needle could result in infection with such diseases. Because the hypodermic needle is frequently used during times of emergency or high stress, it is highly desirable that the needle be immediately shielded after usage in a reliable and efficient manner which provides a high degree of protection from accidental puncture.

A wide variety of different types of devices for shielding a hypodermic needle against inadvertent needle exposure have been advanced. Protective cap-like members for enclosing the sharp end of the needle are incorporated into a number of shield devices. Mitchell U.S. Pat. No. 4,631,057 discloses a shielded needle wherein a needle guard is mounted on the body of a hypodermic syringe. The needle guard moves from the retracted position at which the needle is exposed for usage to an extended position at which the guard shields the needle. The needle guard can be locked in the extended position by inter-locking members carried by the needle guard and a collar which is mounted on the body of the syringe.

Sampson et al U.S. Pat. No. 4,573,976 discloses a shielded needle wherein a needle guard is mounted on the body of the syringe. In an extended position, the needle guard obstructs access to the point of the needle. In a retracted guard position, the point of the needle is exposed for usage. The guard may be releasably retained in a retracted position. Interlocking members on the syringe body are responsive to generally axial movement of the guard to the extended position to prevent reverse movement of the guard toward the retracted position.

In U.S. patent application Ser. No. 093,750, filed on Sept. 8, 1987, entitled "Protective Sheath for Hypodermic Needle", a new and improved protective needle sheath for a hypodermic needle comprises a protective shield assembly which is suitably mounted to the base of the hypodermic needle for shielding the needle point in an extended axial position. The protective shield assembly is axially spaced from the needle point in the retracted position to permit exposure of the needle. In one embodiment, the shield assembly comprises a pair of telescopic concentric, generally cylindrical shields. A mounting flange projects transversely from the needle base. The inner shield has a generally cylindrical surface which axially slides across the peripheral edge of the mounting flange. The sleeve has an end-wall portion and an interior locking means engagable with the flange to lock the inner shield in a fixed axial position wherein the shield encloses a portion of the needle. A radially projecting lock ring is positioned at the opposite distal end of the inner shield. The outer shield has a generally cylindrical surface which axially slides across the peripheral edge of the ring. At a proximal end of the second shield, an interior locking means is engagable with the lock ring to lock the outer shield in fixed axial position with the inner shield whereby the outer shield encloses the needle point and a portion of the needle. In one disclosed embodiment, a flap extends interiorily to the protective guide sleeve. The flap slides along the needle and obstructs axial access to the sharpened needle point in the extended position of the protective shield.

In U.S. application No. 140,566, filed on Jan. 4, 1988, and entitled "Corrugated Protective Sheath for Hypodermic Needle", a protective sheath is mounted to the base of the needle. The protective sheath has a flexible corrugated form which is expandable from a retracted, folded configuration to an extended expanded configuration for shielding the needle point. One end of the protective sheath is anchored in a fixed relationship with the base of the needle. A flap-like member extends interiorily at the opposing leading portion of the shield. In the extended position, the flap cooperates with the sheath to obstruct access to the sharpened needle point to thereby prevent inadvertent puncture.

SUMMARY OF THE INVENTION

Briefly stated, one embodiment of the invention is in the form of a protective hypodermic needle cover assembly for a needle having a base and terminating in a sharpened point. A guide member transversely projects from the needle base and defines a pair of diametrically-spaced slots. A protective shield comprising a cap-like member defining a needle opening is adapted for protectively shielding the needle point in an extended protective position. The needle extends through the opening to expose the needle point in the retracted position. A pair of guide rods extend from the protective cap-like member. The guide rods are received in the slots so that the rods move through the slots when the protective shield member is displaced from the retracted to protective positions with the rods connecting the protective shield to the hypodermic needle in the protective position. A protective flap extends from the cap-like member and is interposed between the opening and the needle in the extended protective position. The rods may interact with the guide member to spring load the cap-like member for maintaining the protected position. Serrations project from the rods and interact with the guide member to prevent retraction of the cap-like member. Stops are connected to the rods to limit the travel of the rods through the slots.

In another embodiment of the invention, a protective foldable sheath is mounted to the needle. A protected cover at the distal end of the sheath defines a needle opening. A guide member projects diametrally from the needle mounting base to define a pair of diametrically-spaced slots. Guide rods having serrations are mounted to the sheath cover and are slidably receivable in the slots for unidirectionally guiding the sheath to the protective mode.

In a third embodiment of the invention, an extendable shield means comprises a plurality of telescopic shield sections. One of the shield sections forms an enclosure having an exteriorly disposed peripheral groove. Another of the shield sections forms an enclosure which is dimensioned to enclose the first shield section and is axially slidable along the first shield section to enclose the sharpened needle point in an extended axial position. The second shield section further comprises a radial projection which is engagable in the groove to lock the shields in the extended position. Diametral tabs extend from the outer most shield section to facilitate moving the cover to the protective mode.

An object of the invention is to provide a new and improved protective cover for a hypodermic needle.

Another object of the invention is to provide a new and improved protective cover of efficient construction which can be easily, manually expanded from a folded retractable position to an expanded, extended protective mode after needle usage for obstructing access to the sharpened end of a hypodermic needle.

Another object of the invention is to provide a new and improved protective cover of inexpensive construction which is relatively easy to manufacture and to assemble on a hypodermic needle.

A further object of the invention is to provide a new and improved protective cover assembly which is easily positionable to lock a protective needle cover in the protective position.

Other objects and advantages of the invention will become apparent from the drawing and the specification.

BRIEF DESCRIPTION OF THE DRAWINGS

FIG. 1 is a side elevational view, partly in phantom, of a hypodermic syringe and a protective cover assembly of the present invention, said cover assembly being positioned in a retracted mode wherein the syringe needle is exposed;

FIG. 2 is an enlarged fragmentary, side elevational view, partly in section and partly broken away, of the hypodermic syringe and the protective cover assembly of FIG. 1;

FIG. 3 is an enlarged fragmentary, side elevational view, partly in section, of the hypodermic syringe and the protective cover assembly of FIG. 1, said cover assembly being positioned in a protective mode;

FIG. 4 is a cross-sectional view of the hypodermic syringe and protective cover assembly of FIG. 3 taken along the line 4—4 thereof;

FIG. 5 is a fragmentary, side elevational view, partly in section, of a hypodermic syringe and a second embodiment of a protective cover assembly in accordance with the present invention, said cover assembly being positioned in a retracted mode wherein the syringe needle is exposed;

FIG. 6 is a side elevational view, partly in section, of the hypodermic syringe and protective cover assembly of FIG. 5, said cover assembly being positioned in the protective mode;

FIG. 7 is a cross-sectional view of the hypodermic syringe and protective cover assembly of FIG. 5 taken along the line 7—7 thereof;

DETAILED DESCRIPTION OF THE INVENTION

Figure 9:
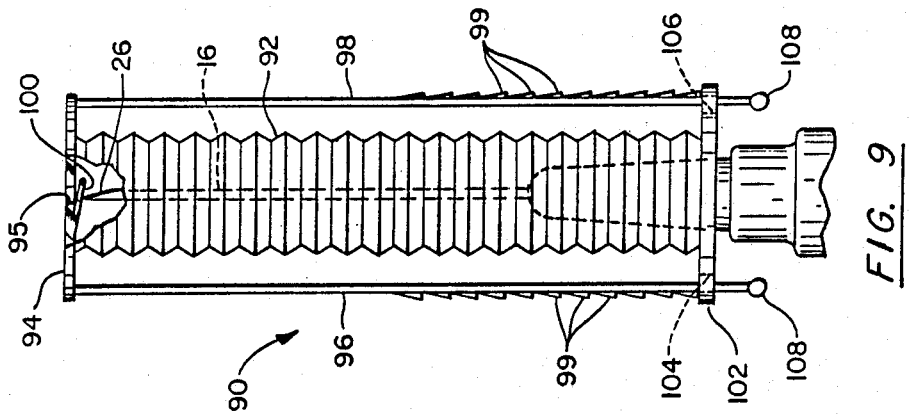
FIG. 9 is a fragmentary side elevational view, partly broken away, partly in section, and partly in phantom, of the hypodermic syringe and protective cover assembly of FIG. 8, the cover assembly being positioned in a protective mode.

With reference to the drawings wherein like numerals represent like parts throughout the Figures, a hypodermic syringe is designated generally by the numeral 10 in FIG. 1. Except for the modifications described herein, syringe 10 has a generally conventional form and function. The hypodermic syringe 10 mounts a protective cover assembly 12 in accordance with the present invention. Syringe 10 generally comprises a main syringe body 14 and a hypodermic needle 16. The protective cover assembly 12 is adapted for protecting the distal sharpened end of the syringe hypodermic needle 16 after usage of the syringe. The protective cover assembly 12 has applicability for syringes, catheters and like devices which are employed for injecting substances and/or drawing specimens. Accordingly, the specific illustrated embodiments of syringe 10 and hypodermic needle 16 with which the invention is illustrated and described may have numerous embodiments and configurations.

The main syringe body 14 includes a generally cylindrical barrel or vial 20 which receives the substance injected by the syringe and/or the specimen withdrawn by the syringe. The vial 20 constitutes the principal body portion of the syringe. A needle socket 22 or anchoring head is formed at one end of the syringe body for receiving and mounting the hypodermic needle 16.

The hypodermic needle 16 includes an integral upper mounting base 24 which tapers into a cannula-like head having a distal sharpened point 26. A mounting base 24 fixedly mounts or is anchored by the socket 22 of the syringe body. The cannula defines an axial fluid passageway which extends from the vial through the needle and opens through the sharpened point end in a conventional manner.

A wide variety of means for fixing or mounting the base 24 of the hypodermic needle to the mounting body of the syringe or other device may be provided. The hypodermic needle 16 may be mounted at the syringe body by a molding process wherein the socket or anchoring is integrally formed around the needle base. Alternatively, a Luer-type connector (not illustrated) may connect the mounting base with the main syringe body.

With reference to FIGS. 1 through 4, the protective cover assembly 12 comprises a cap 30 having an interiorly projecting, integral protective flap 32 and a central axial aperture 34. The aperture 34 is adapted and dimensioned so that the needle extends therethrough in the retracted mode illustrated in FIGS. 1 and 2. A circumferential annular anchoring collar 36 extends outwardly (generally radially) at the proximal end of the cap. The cap 30 is preferably composed plastic or other inexpensive molded material. The cap 30 is dimensioned to partially enclose a portion of the needle base 24.

A slotted wing 40 extends diametrically of the needle base. The wing 40 defines a pair of diametrically-spaced apertures 42 and 44. Guide rods 46 and 48 are fixed at diametrically located positions of the collar 36 and extend through the apertures 42 and 44. The guide rods 46 and 48 function to guide the cap 30 to the protective position and to retain the cap to the syringe. In addition, the guide rods may have sufficient resilience so that the rods are spring loaded against the wing 40 to thereby maintain the protective position illustrated in FIG. 3. The guide rods may also have a series of longitudinally spaced serrations 52 which are engageable against aperture-defining portions of the wings to prevent the cap from being redisplaced to the retracted position. The apertures 42 and 44 and the serrations 52 are dimensioned to allow generally unidirectional movement to the extended protective position. A pair of knobs 49 having diameters greater than the corresponding diameters of the apertures 42 and 44 function as stops to limit the axial travel of the guide rods through the apertures.

As best illustrated in FIG. 2 at the retracted position wherein the hypodermic needle is exposed, the protective flap 32 is bent against the distal portion of the needle base 24. When the protective cap 30 is manually moved to the protective position illustrated in FIG. 3, the flap 32 resiliently slidably engages along the needle 16 until the flap clears the needle point 26 at the extended position of FIG. 3. The flap 32 springs to an extended configuration for inter-positioning between the aperture 30 of the cap and the needle point 26, thus providing a secondary needle shield. The guide rods 46 and 48 are spring biased and the serrations 52 engage against opposing aperture defining portions of the wing 40 to spring load the cap at the protective position.

With reference to FIGS. 5 through 7, a second embodiment of a protective cap assembly is generally designated by the numral 60. Cap assembly 60 comprises three telescoping shield sections 62, 64, and 66, which in a compact retracted nested configuration of FIG. 5, allow the needle 16 to be exposed for usage. The sections 62, 64 and 66 may have a wide variety of shapes. The sections preferably have a semi-rigid resilient structure and may be formed from plastic or similar materials. Section 62 is anchored or connected to the needle base 24. Each of the sections have distal end panels which define respective central apertures 63, 65 and 67. The needle extends through the apertures 63, 65 and 67 in the retracted positions. The needle also extends through apertures 63 and 65 in the expanded protective position as illustrated in FIG. 6.

Sections 62 and 64 have peripheral circumferentially extending locking grooves 71 and 73, respectively, proximate the distal exterior ends of the sections. Each of the sections 64 and 66 have corresponding interiorily projecting tongues 72 and 74, respectively, which are receivable in the locking grooves 71 and 73, respectively, to secure the shield sections in the protective expanded position of FIG. 6. The sections have sufficient resiliency so that the tongues slide along the exterior surface of a corresponding interiorly adjacent section 68 and snap into the grooves at the extreme protective position.

The outer shield section 66 which essentially encloses the sharpened needle point 26 also includes an integral protective flap 68 which rides along the needle 16 and is interposed between the aperture 67 and the sharpened needle point 26 in the protective mode in a manner similar to that described in relation to flap 32. In addition, the outer section 66 has a pair of diametral integral wing-like tabs 80 and 82 which facilitate the transformation of the shield to the telescoping protective mode.

Figure 8:
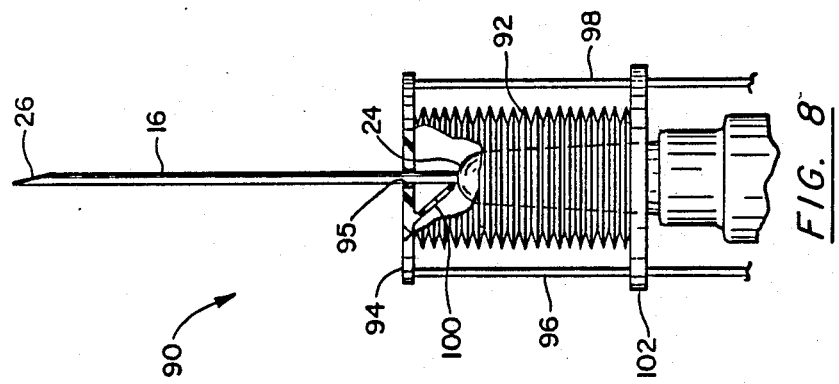
FIG. 8 is a fragmentary side elevational view, partly in section and partly broken away, of a hypodermic syringe and a third embodiment of protective cover assembly in accordance with the present invention, said cover assembly being positioned in a retracted mode wherein the syringe needle is exposed.

With additional reference to FIGS. 8 and 9, a third embodiment of a protective cover assembly is generally designated with the numeral 90. Protective cover assembly 90 includes a corrugated sheath 92 and an end plate 94 which is mounted at the distal end of the corrugated sheath. The diameter of the end plate 94 is greater than the diameter of the sheath 92. The end plate 94 defines a central aperture 95 through which the needle extends in the retracted position. A pair of guide rods 96 and 98 are anchored at outer diametral positions of the end plate 94. An integral protective flap 100 also extends interiorily from the end plate 94. Flap 100 is similar in form and function to previously described flaps 32 and 68. It will be appreciated that the end plate 94 functions as the primary needle shield and the flap 100 functions as a secondary or auxiliary needle shield. Flap 100 resiliently slidably engages along the needle 16 for interpositioning between the end of the end plate aperture 95 and the sharpened needle point 26 as best illustrated in FIG. 9.

A guide bar 102 is fastened to the needle base and extends radially therefrom. The guide bar defines a pair of diametrically-spaced slots or apertures 104 and 106 which receive the guide rods 96 and 98. The guide rods include a series of longitudinally spaced serrations 99 which function in a manner similar to serrations 52 to form a one way stop for maintaining the protective cover in the extended protective mode. A pair of knobs 108 are mounted at the end of the guide rods to limit the travel of the end plate 94 relative to the needle base. Th guide rods may also function to spring bias the protective cover in the protective mode as best illustrated in FIG. 9.

While preferred embodiments of the foregoing invention have been set forth for purposes of illustration, the foregoing description should not be deemed a limitation of the invention herein. Accordingly, various modifications, adaptations, and alternatives may occur to one skilled in the art without departing from the spirit and the scope of the present invention.

What is claimed is:

1. A protective hypodermic needle cover assembly comprising:
   hypodermic needle means comprising a mounting base and a needle connecting said base and terminating in a sharpened point axially spaced from said base, said base comprising a transversely projecting guide means defining a pair of apertures;
   protective shield means mounted to said base for protectively shielding said needle point in an extended protective position, said shield means comprising a cap-like member defining a needle opening, said needle extending through said opening to expose said needle point in a retracted position; and
   a pair of guide rods extending from said protective shield means and received in said apertures so that the rods move through said apertures when the protective shield means is displaced from the retracted to protective positions, said rods connecting said protective shield means to said hypodermic means in the protective position.

2. The protective cover assembly of claim 1 further comprising a protective flap interiorly extending from said cap-like member and interposed between said opening and needle point in the extende position.

3. The protective cover assembly of claim 1 wherein said cap-like member further comprises a radially extending shoulder and said rods are fastened to said shoulder.

4. The protective cover assembly of claim 1 wherein said rods interact with said guide means to spring load the cap-like member for maintaining the protective position.

5. The protective cover assembly of claim 1 further comprising stop means for limiting the travel of the rods through said slots.

6. The protective cover assembly of claim 1 wherein a series of longitudinally spaced serrations project from said rods, said serrations being engageable with said guide means for maintaining said cap-like member in the protective position.

7. A protective hypodermic needle cover assembly comprising:
   needle means comprising a mounting base and a needle connecting said base and terminating in a sharpened point axially spaced from the base;
   protective sheath means mounted to said needle means for protecting said needle point in a protective mode, said sheath means comprising a foldable sheath and a protective covering at the distal end thereof, said cover defining an opening, said foldable sheath connecting to said needle base at a proximal end, said sheath having a corrugated form which is axially expandable from a collapsed folded position wherein said needle projects through said opening to permit exposure of the needle point to an extended protective position wherein said sheath surrounds said needle point;
   guide means projecting diametrally from said mounting base, said guide means defining a pair of diametrally-spaced apertures; and
   guide rod means mounted to said covering and slidably receivable in said apertures for guiding said sheath means to the protective mode.

8. The protective cover assembly of claim 7 wherein said guide rod means interact with said guide means to bias said sheath in the protective mode.

9. The protective cover assembly of claim 7 wherein said guide rod means further comprises a pair of rods and further comprising stops extending from said rods, said stops having a diameter which is greater than the corresponding diameters of the apertures.

10. The protective cover assembly of claim 7 further comprising a protective flap extending interiorly from said protective covering and positionable between said covering and said needle point in the protective mode.

11. The protective cover assembly of claim 7 wherein said guide rods means further comprise unidirectional means for engagement with said guide means to prevent displacement of said sheath means to the folded position.

12. The protective cover assembly of claim 11 wherein said unidirectional means comprise a plurality of serrations.

* * * * *